(12) United States Patent
Li et al.

(10) Patent No.: US 12,415,022 B1
(45) Date of Patent: *Sep. 16, 2025

(54) FLOW DISTRIBUTION STRUCTURE FOR A BLOOD PROCESSING UNIT

(71) Applicant: Chinabridge (Shenzhen) Medical Technology Co., Ltd., Shenzhen (CN)

(72) Inventors: Yijiang Li, Shenzhen (CN); Weiyun Wang, Shenzhen (CN)

(73) Assignee: CHINABRIDGE (SHENZHEN) MEDICAL TECHNOLOGY CO., LTD., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/776,156

(22) Filed: Jul. 17, 2024

Related U.S. Application Data

(63) Continuation of application No. 18/655,107, filed on May 3, 2024.

(51) Int. Cl.
*A61M 1/16* (2006.01)

(52) U.S. Cl.
CPC ........ *A61M 1/1698* (2013.01); *A61M 1/1623* (2014.02)

(58) Field of Classification Search
CPC .. A61M 1/1698; A61M 2206/16; F28F 13/06; F28D 7/1623; B01D 2313/08; B01D 2313/19
See application file for complete search history.

(56) References Cited

U.S. PATENT DOCUMENTS

| 4,876,066 A | 10/1989 | Bringham et al. |
| 6,053,967 A * | 4/2000 | Heilmann .......... B01D 19/0057 96/216 |
| 2012/0193289 A1* | 8/2012 | Cloutier .............. A61M 1/1698 422/46 |
| 2013/0094997 A1* | 4/2013 | Wang ................... A61M 60/117 422/48 |

FOREIGN PATENT DOCUMENTS

| CN | 107432960 B | 12/2017 |
| CN | 115554505 A * | 1/2023 |
| EP | 2667908 B1 | 6/2016 |

* cited by examiner

*Primary Examiner* — Nicholas J. Weiss
*Assistant Examiner* — Seth Han
(74) *Attorney, Agent, or Firm* — Nelson Mullins Riley & Scarborough LLP

(57) ABSTRACT

A blood processing unit for use in connection with extracorporeal blood circulation includes a housing including a blood inlet, an upper end cap defining a central inlet opening, and a blood outlet. Blood flows along a blood flow path between the blood inlet and the blood outlet. A plurality of layers of hollow fibers are disposed inside the housing and along the blood flow path. The hollow fibers are fluidly coupled to a gas inlet port and a gas outlet port. The device includes a flow distribution structure for modifying blood flowing along the blood flow path. The structure includes a body having a distal end, a proximal end, and an outer surface extending between the distal end and the proximal end. An inlet configured for connecting with the upper end cap is spaced from the proximal end. A plurality of curved dividers extend between the inlet and the body.

18 Claims, 13 Drawing Sheets

FLOW DISTRIBUTION STRUCTURE FOR A BLOOD PROCESSING UNIT

TECHNICAL FIELD

This disclosure relates to the field of devices for extracorporeal circulation of blood. More specifically, the disclosure relates to some important components of the extracorporeal circuit, such as the oxygenation device, in particular flow distribution structures for use in the oxygenation device.

BACKGROUND

Blood extracorporeal circuits may include a blood processing unit, which may include one or more of an oxygenator module to exchange oxygen and carbon dioxide between blood and a gas mixture and a heat exchanger module to exchange heat between blood and a heating or cooling fluid through the walls of semipermeable hollow fiber membranes. Such circuits also include other elements like a pump for providing a certain blood flow through the circuit and sensors measuring quantities, among others, like blood pressures, flow rate, temperatures, oxygen saturations and oxygen and carbon dioxide partial pressures. Blood contacts the outside surfaces of the hollow fibers, while the gas mixture and the heating/cooling fluid (e.g., a water solution) are circulated inside the hollow fiber lumens. In the devices using this technology, the hollow fibers may be organized in different ways. They may be in a single or multifilament form which is woven around a core or may be structured in woven mats wound around a core (to form a so-called "wound" oxygenator type) or stacked in parallel mat layers on top of one another without a core (to form a so-called "stacked" oxygenator type). Various examples of this technology are well known in the technical field.

As far as the blood pump it may be of roller, or centrifugal types. In the latter case, the pump rotor may be levitated and kept floating by means of a magnetic field, which results in low friction operation and hence reduced hemolysis rate, particularly necessary in long term perfusion procedures like in ECMO (ExtraCorporeal Membrane Oxygenation), lasting several days, if not a few weeks, of continuous extracorporeal heart/lung support of the patient. In ECMO, very often the extracorporeal circuit needs to be moved with the patient from one hospital department to another and thus it's important that it be as much simplified, compact and lightweight as possible.

SUMMARY

Example 1 includes a blood oxygenation device for use in connection with extracorporeal blood circulation. The device includes a housing including a blood inlet, an upper end cap defining a central inlet opening, and a blood outlet. Blood flows along a blood flow path between the blood inlet and the blood outlet. A plurality of layers of hollow fibers are disposed inside the housing and along the blood flow path. The hollow fibers are fluidly coupled to a gas inlet port and a gas outlet port. The device includes a flow distribution structure for modifying blood flowing along the blood flow path. The structure includes a body having a distal end, a proximal end, and an outer surface extending between the distal end and the proximal end, wherein the body includes a tapered proximal portion extending from the proximal end towards the distal end. An inlet is spaced from the proximal end, the inlet configured for connecting with the upper end cap. A plurality of curved dividers are coupled to and extend between the inlet and the tapered proximal portion.

Example 2 is the device of Example 1, wherein the body further includes a distal portion and a first length of the tapered proximal portion is less than a second length of the distal portion.

Example 3 is the device of Example 2, wherein the plurality of curved dividers spiral in the direction of blood flow from the inlet towards the tapered proximal portion.

Example 4 is the device of Example 3, wherein the spiral has an angle in the range of about 5 degrees to 50 degrees.

Example 5 is the device of Example 3, wherein the tapered proximal end tapers non-linearly.

Example 6 is the device of Example 1, wherein the inlet includes a reduced diameter portion and a step configured to mate with the central inlet opening of the upper end cap.

Example 7 is the device of Example 1, wherein the body is hollow from the distal end to the proximal end.

Example 8 is the device of Example 7, wherein an inner surface of the body includes a plurality of ribs for connecting the flow distribution structure to a fixture for fixing a location of the blood processing unit.

Example 9 is the device of Example 8, wherein the plurality of ribs extend from the distal end to an inner surface of a tapered proximal portion.

Example 10 is the device of Example 1, wherein the plurality of dividers includes at least three dividers.

Example 11 is the device of Example 1, wherein the plurality of curved dividers each include a first end connected to the inlet and a second end connected to the body.

Example 12 is the device of claim 11, wherein the body of the flow distribution structure includes a tapered proximal portion extending from the proximal end towards the distal end, the tapered proximal portion having an upper half and a lower half, wherein the second end of each of the plurality of curved dividers is joined to the tapered proximal portion upper half.

Example 13 is a flow distribution structure for use with a blood oxygenation device. The structure includes a body having a distal end, a proximal end, and a tapered proximal portion extending from the proximal end towards the distal end. An inlet is spaced from the proximal end. The inlet is configured for connecting with an upper end cap of the blood oxygenation device. A plurality of dividers are positioned between the inlet and the body. The plurality of dividers spiral from the inlet towards the tapered proximal portion. In use, blood flows through the inlet and over an outer surface of the body.

Example 14 is the structure of Example 13, wherein the spiral has an angle in the range of about 5 degrees to 50 degrees.

Example 15 is the structure of Example 13, wherein an inner surface of the body includes a plurality of ribs for connecting the flow distribution structure to a fixture for fixing a location of the blood processing unit.

Example 16 is the structure of Example 13, wherein the plurality of curved dividers each include a first end connected to the inlet and a second end connected to the body.

Example 17 is the structure of Example 16, wherein the body of the flow distribution structure includes a tapered proximal portion extending from the proximal end towards the distal end, the tapered proximal portion having an upper half and a lower half, wherein the second end of each of the plurality of curved dividers is joined to the tapered proximal portion upper half.

Example 18 is a flow distribution structure for use with a blood oxygenation device. The structure includes a body having a distal end, a proximal end, and a tapered proximal portion extending from the proximal end towards the distal end. An inlet is spaced from the proximal end. The inlet is configured for connecting with an upper end cap of the blood oxygenation device. A plurality of dividers are positioned between the inlet and the body. A plurality of ribs extend from the tapered proximal portion towards the distal end. In use, blood flows through the inlet and over an outer surface of the body.

Example 19 is the structure of Example 18, wherein the body includes a flared portion extending from the distal end towards the proximal end.

Example 20 is the structure of Example 18, wherein the plurality of dividers includes at least three dividers and the plurality of ribs includes at least three ribs.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
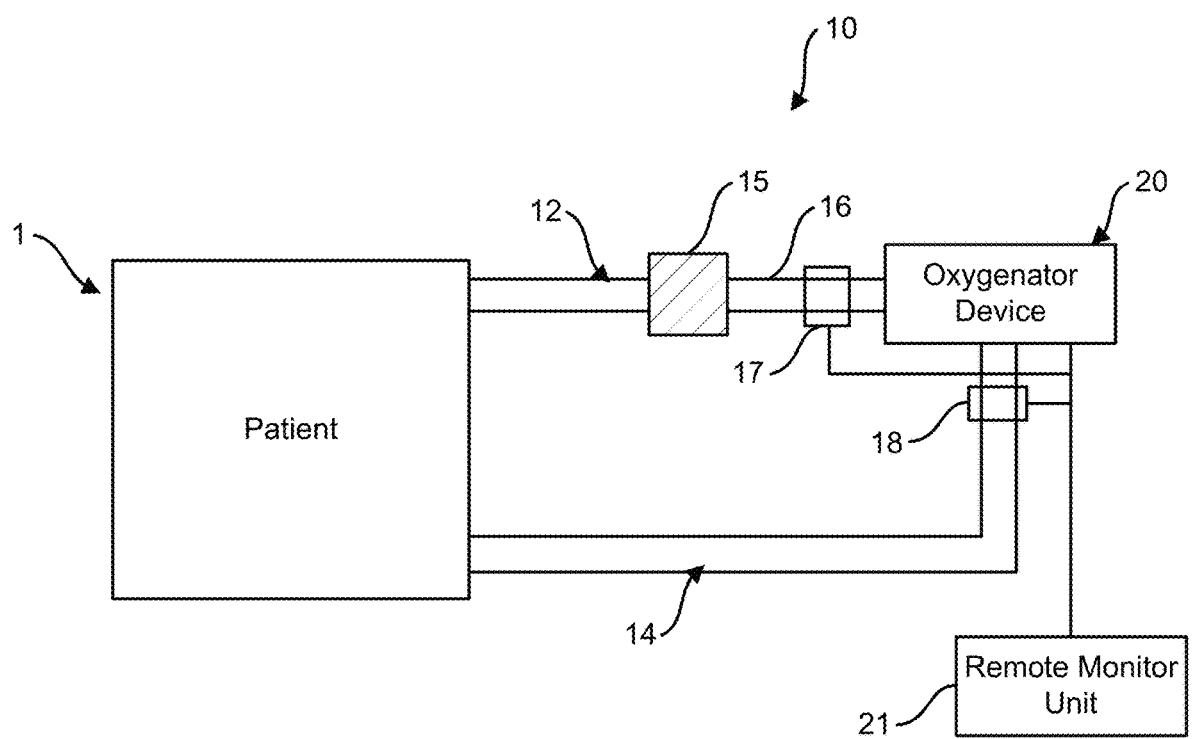
FIG. 1 is a schematic view of a patient undergoing extracorporeal blood circulation.

While the invention is amenable to various modifications and alternative forms, specific embodiments have been shown by way of example in the drawings and are described in detail below. The intention, however, is not to limit the invention to the embodiments described. On the contrary, the invention is intended to cover all modifications, equivalents, and alternatives falling within the scope of the invention as defined by the appended claims.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, and/or dimensions are provided for selected elements. Those skilled in the art will recognize that many of the noted examples have a variety of suitable alternatives.

As the terms are used herein with respect to measurements (e.g., dimensions, characteristics, attributes, components, etc.), and ranges thereof, of tangible things (e.g., products, inventory, etc.) and/or intangible things (e.g., data, electronic representations of currency, accounts, information, portions of things (e.g., percentages, fractions), calculations, data models, dynamic system models, algorithms, parameters, etc.), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error; differences in measurement and/or manufacturing equipment calibration; human error in reading and/or setting measurements; adjustments made to optimize performance and/or structural parameters in view of other measurements (e.g., measurements associated with other things); particular implementation scenarios; imprecise adjustment and/or manipulation of things, settings, and/or measurements by a person, a computing device, and/or a machine; system tolerances; control loops; machine-learning; foreseeable variations (e.g., statistically insignificant variations, chaotic variations, system and/or model instabilities, etc.); preferences; and/or the like.

Although illustrative methods may be represented by one or more drawings (e.g., flow diagrams, communication flows, etc.), the drawings should not be interpreted as implying any requirement of, or specific order among or between, various steps disclosed herein. However, certain some embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

As used herein, the term "based on" is not meant to be restrictive, but rather indicates that a determination, identification, prediction, calculation, and/or the like, is performed by using, at least, the term following "based on" as an input. For example, predicting an outcome based on a particular piece of information may additionally, or alternatively, base the same determination on another piece of information.

FIG. 1 is a schematic view of an extracorporeal blood circulation system 10 (also referred to herein as an extracorporeal circuit 10) for supporting a patient 1 requiring extracorporeal blood circulation. In various embodiments, the patient 1 is connected through a first tubing 12 (also called a venous line) to the extracorporeal blood circuit 10 including a pump 15 to cause blood to be transferred from the patient 1, through the first tubing 12 and 16, to a mass transfer device 20, commonly referred to as a blood processing unit or as an oxygenation 20. Note that the blood processing unit 20 includes one or both of an oxygenation module to exchange oxygen and carbon dioxide between blood and a gas mixture and a heat exchanger module to exchange heat between blood and a heating or cooling fluid through the walls of semipermeable hollow fiber membranes.

The system 10 further includes a second tubing 14 (also called an arterial line) that extends from the oxygenator 20 to the patient 1 for transferring blood that has been circulated within the pump 15 and oxygenator 20 back to the patient 1. The extracorporeal circuit 10 includes a plurality of sensors which measure parameters like blood pressures, flow rate, temperatures, hematocrit, oxygen saturation and oxygen and carbon dioxide partial pressures of blood, that must be kept under control during the perfusion process. In general, and not exclusively, such sensors may be located pre- and/or post-oxygenator, depending on whether the quantities must be measured on the venous or the arterial side. In FIG. 1, a group of venous side sensors 17 and a group of arterial side sensors 18 are schematically shown. They may be in direct contact with blood or may measure the quantities from the tubing outside and are electrically connected to a separate and remote control and monitoring unit 21 under operator (e.g., a perfusionist) control by means of an appropriate control system. In various embodiments, oxygen ($O_2$) and carbon dioxide ($CO_2$) are exchanged between blood and a gas mixture within the oxygenator device 20, as will be described further herein. The oxygenator device 20, in certain embodiments, is also configured for exchanging temperature (hot or cool temperatures) between the blood and heating/cooling (H/C) fluid within the oxygenator device 20. In some embodiments, the H/C fluid is water or a water solution.

Figure 2:
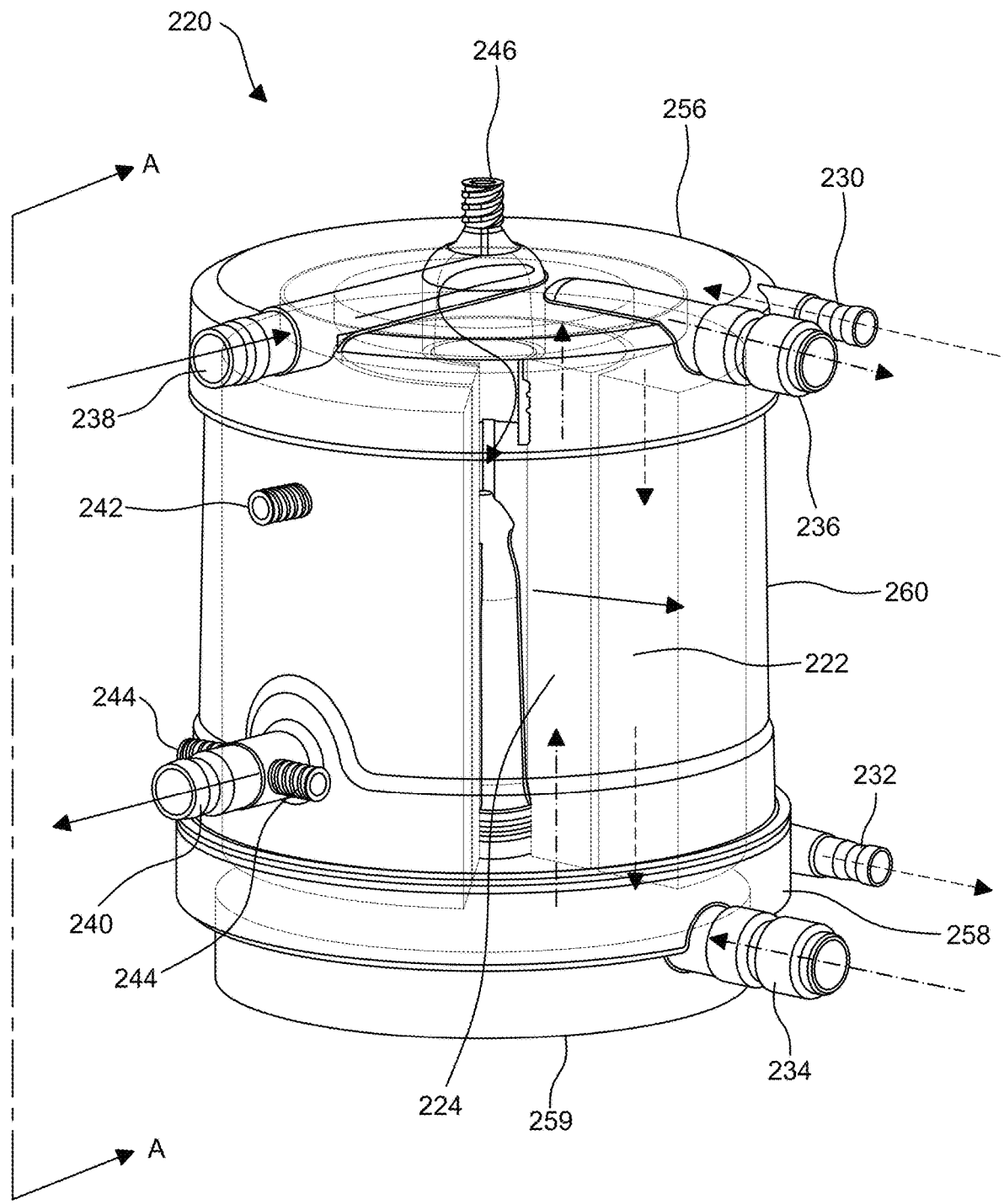
FIG. 2 is a perspective view of a blood oxygenation device, in accordance with an embodiment of the disclosure.

FIG. 2 is a perspective view of an oxygenation device 220 having an oxygenator module 222 and a heat exchanger module 224. The oxygenation device 220 includes an upper end cap 256, a lower end cap 258, and a cylindrical body 260 located between the upper end cap 256 and the lower end cap 258. In various embodiments, the oxygenation device 220 includes a gas inlet port 230 configured for receiving a gas mixture, a gas outlet port 232 configured for exporting a gas mixture, a H/C fluid inlet port 234 for receiving H/C fluid, for example water, an H/C fluid outlet port 236 for exporting H/C fluid, a blood inlet port 238 for receiving blood from the patient 1 through the tubing 16, and a blood outlet port 240 for exporting blood from the oxygenation device 220 back to the patient 1 through the tubing 14. The oxygenation device 220 further includes a pair of arterial sampling ports 244, a purging port 242, and an upper venous port 246.

The upper end cap 256 includes the blood inlet port 238 which is configured for receiving blood from tubing 16. The cylindrical body 260 includes the blood outlet port 240 for providing an exit for the blood to return to the patient 1 through the tubing 14. The gas inlet port 230 and the H/C fluid outlet port 236 are also integral with the upper end cap 256. The lower end cap 258 includes the H/C fluid inlet port 234 and the gas outlet port 232. At least one purging port 242 may allow for removal of air during an initial priming phase of the oxygenation device 220 prior to use with the patient. During operation, i.e., when blood and gas flow through the device 220, the at least one purging port 242 may be opened for removing entrapped air from blood. Additionally, the at least one purging port 242 may be opened after operation of the device 220, i.e., when blood is no longer flowing through the device 220, to ensure proper emptying of any blood from the device 220 and returning it to the patient. The oxygenation device 220 includes a pedestal 259 positioned on a bottom surface of the lower end cap 258 for supporting and stabilizing the device 220.

Figure 3A:
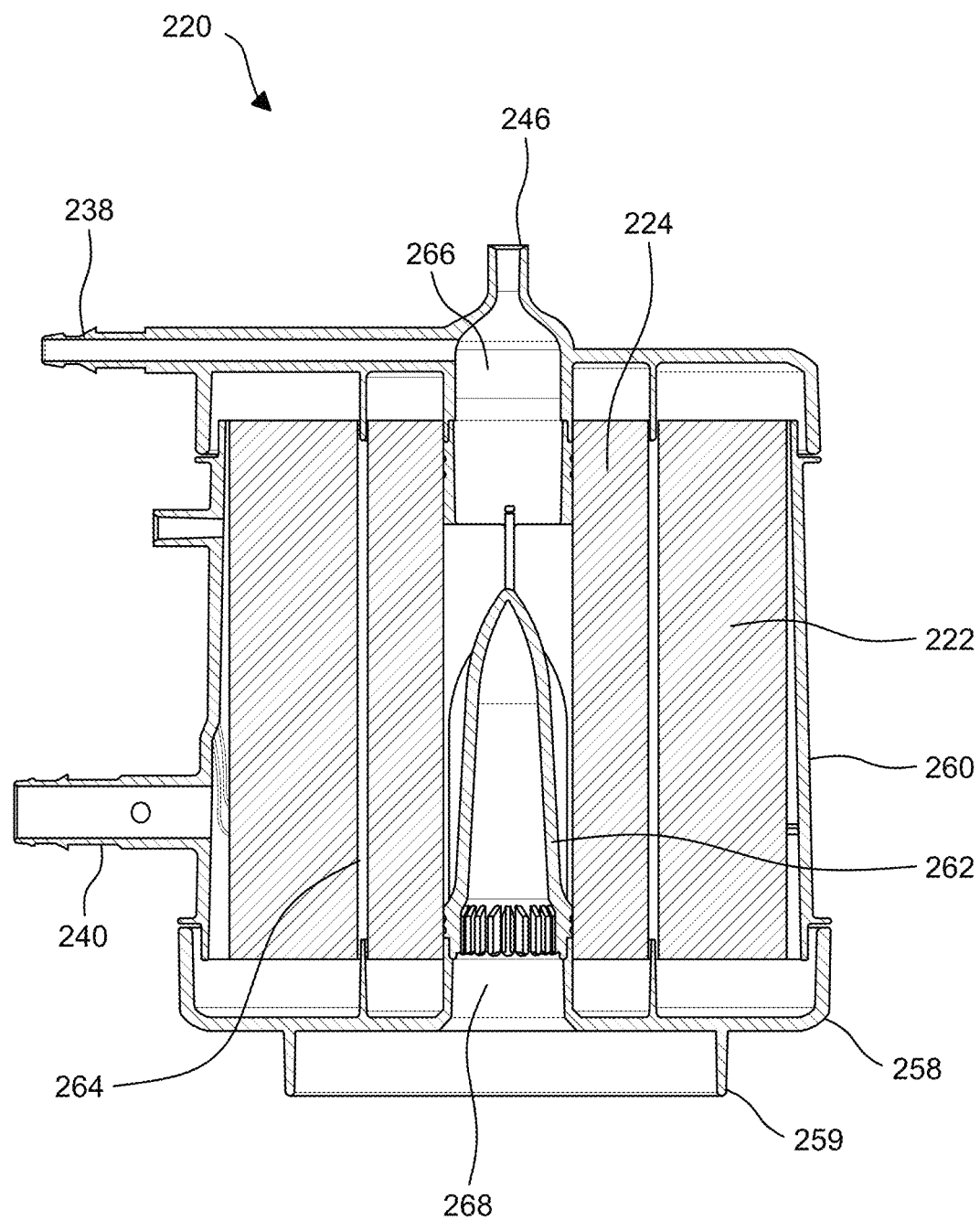
FIG. 3A is a cross-section of the blood oxygenation device taken along line A-A of FIG. 2.

As illustrated in FIG. 3A, the cylindrical body 260 houses a core or flow distribution structure 262, an oxygenator module 222, and a heat exchanger module 224. Both modules 222, 224 are provided with hollow fiber woven mat layers vertically stacked one adjacent to the other. In some embodiments, the woven layers are formed as a continuous double mat layer which is spirally wound around the core of flow distribution structure 262. In some embodiments, the layers of hollow fiber mats are made, for the oxygenator module 222, of polypropylene, or polymethilpentene and, for the heat exchanger module 224, of polyethylene, or polyurethane. They are potted together and to the upper and lower end caps 256, 258 with polyurethane resin and afterwards sliced on their outer surface to cut open the fibers lumens so as to allow water and gas circulation inside the fiber lumens. The woven fibers of the double mat are alternatively angled vs an alignment direction by an angle $\alpha$ and an angle $\beta$ disposed on opposite sides of the alignment direction. Angles $\alpha$ and $\beta$ may be equal, or not, and are each comprised in the range 0 to 25 degrees.

Blood flowing through the oxygenation device 220 is able to come into contact (by interposition of the appropriate hollow fiber membranes in the heat exchanger module 224 and the oxygenator module 222), with the fluid mixtures and the gas mixtures for sufficient heat and gas exchange. The flow distribution structure 262 is located in the center of the cylindrical body 260. The heat exchanger module 224 and the oxygenator module 222 are concentrically positioned around the flow distribution structure 262 and are adjacent one another. The heat exchanger module 224 is located adjacent the flow distribution structure 262 and is separated from the oxygenator module 222 by a separation grid 264 which provides a physical separation between the oxygenator module 222 and the heat exchanger module 224. The separation grid 264 distributes blood flowing past the heat exchanger module 224 towards the oxygenator module 222. In some embodiments, a separation grid 264 is not included between the oxygenator module 222 and the heat exchanger module 224.

Figure 3B:
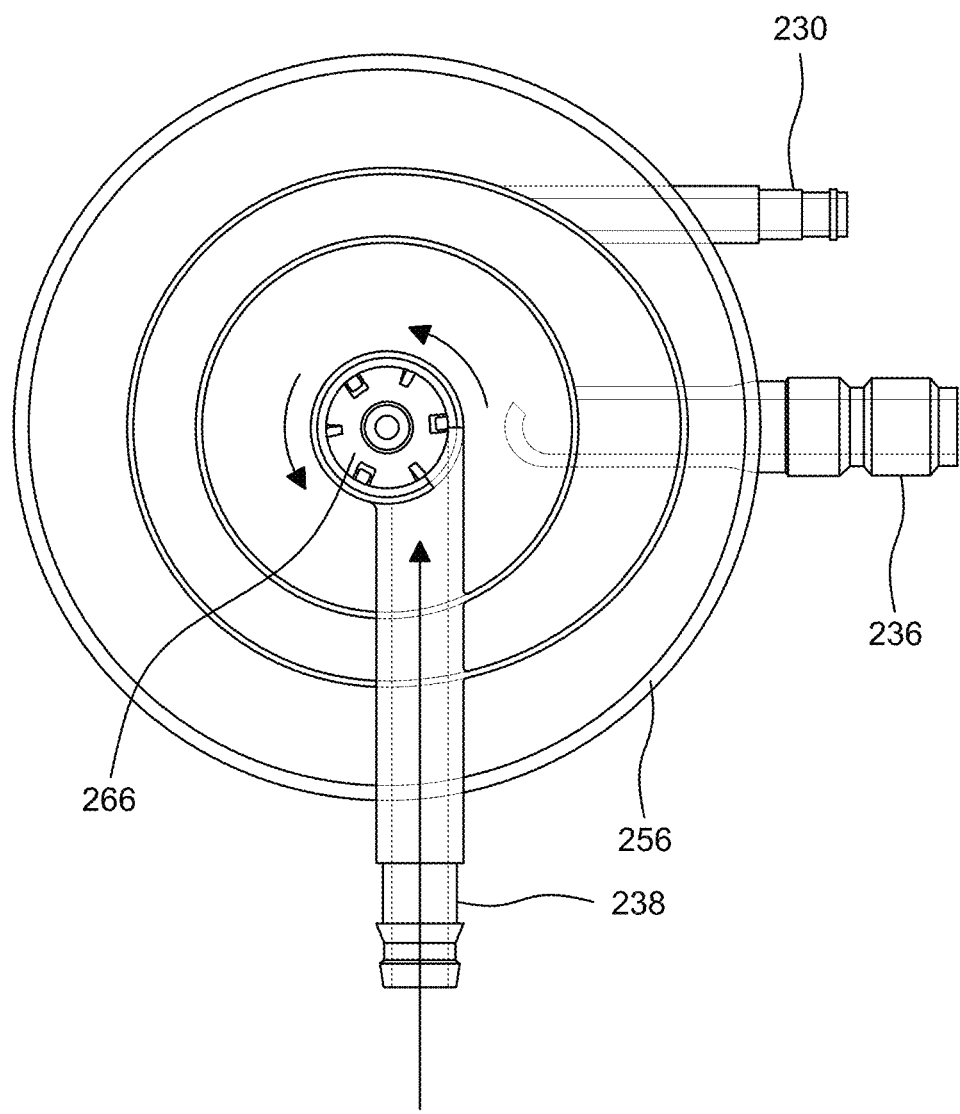
FIG. 3B is a top view of the blood oxygenation device of FIG. 2.

As illustrated in FIG. 3B, blood enters the upper end cap 256 through the blood inlet port 238 and enters a central inlet opening 266 of the upper end cap 256. The blood rotates downward and over the outer surface of the flow distribution structure 262 (see FIG. 3A). As shown, the longitudinal axis of the blood inlet port 238 is offset from the central inlet opening 266. This tangential configuration causes the entering blood to spiral or flow with a generally centrifugal motion.

The flow distribution structure 262 is configured to divide the blood flow into multiple streams for introduction into the heat exchanger module 224. The blood is brought to a desired temperature when passing through the heat exchanger module 224. The blood travels through the separation grid 264 to the oxygenator module 222 where an exchange of oxygen with carbon dioxide takes place. Following oxygenation, the blood is collected at the outer periphery of the interior of the cylindrical body 260 and is directed through the blood outlet port 240 back to the patient 1.

In certain embodiments, the upper end cap 256 and the lower end cap 258 are provided with means to mechanically connect with the cylindrical body 260, for example protrusions configured to fit into corresponding notches. Air tightness between the upper end cap 256, the lower end cap 258, and the cylindrical body 260 may be obtained by resin casting along the circular contact surfaces of the upper end cap 256, the lower end cap 258, and the cylindrical body 260. Alternatively, air tightness between upper end cap 256, the lower end cap 258, and the cylindrical body 260 can be insured by placing one or more seals in recesses configured to be compressed between adjacent contact surfaces.

In some embodiments, the oxygenation device 200 includes pressure sensors integrated in blood inlet port 238 and the blood outlet port 240 and connected by means of a single cable (not shown) to the remote monitoring unit 21. Alternatively, the pressure sensors can include a wireless (e.g., radio-frequency, Bluetooth or Wi-Fi) connection with the remote monitoring unit 21. Any pressure signals from the pressure sensors may be displayed in mmHg (which is the most commonly used unit in cardiac surgery or ECMO applications), shown on a screen in numerical, or graphical form and compared with limits set by the operator, or fixed by the system. If such limits are exceeded, audible and visual alarms may be switched on to attract the operator attention who may decide to start corrective actions. Inlet/outlet pressure values may also be shown as difference between them (i.e., as a pressure drop, ΔP). The pressure drop value may be monitored by activating an alarm, in case it exceeds a set value. It may also be factored into an appropriate functionality of the remote control and monitoring unit to automatically act on the pump speed (i.e., revolutions per minute) so as to maintain the blood flow rate at a constant set value.

Figure 4A:
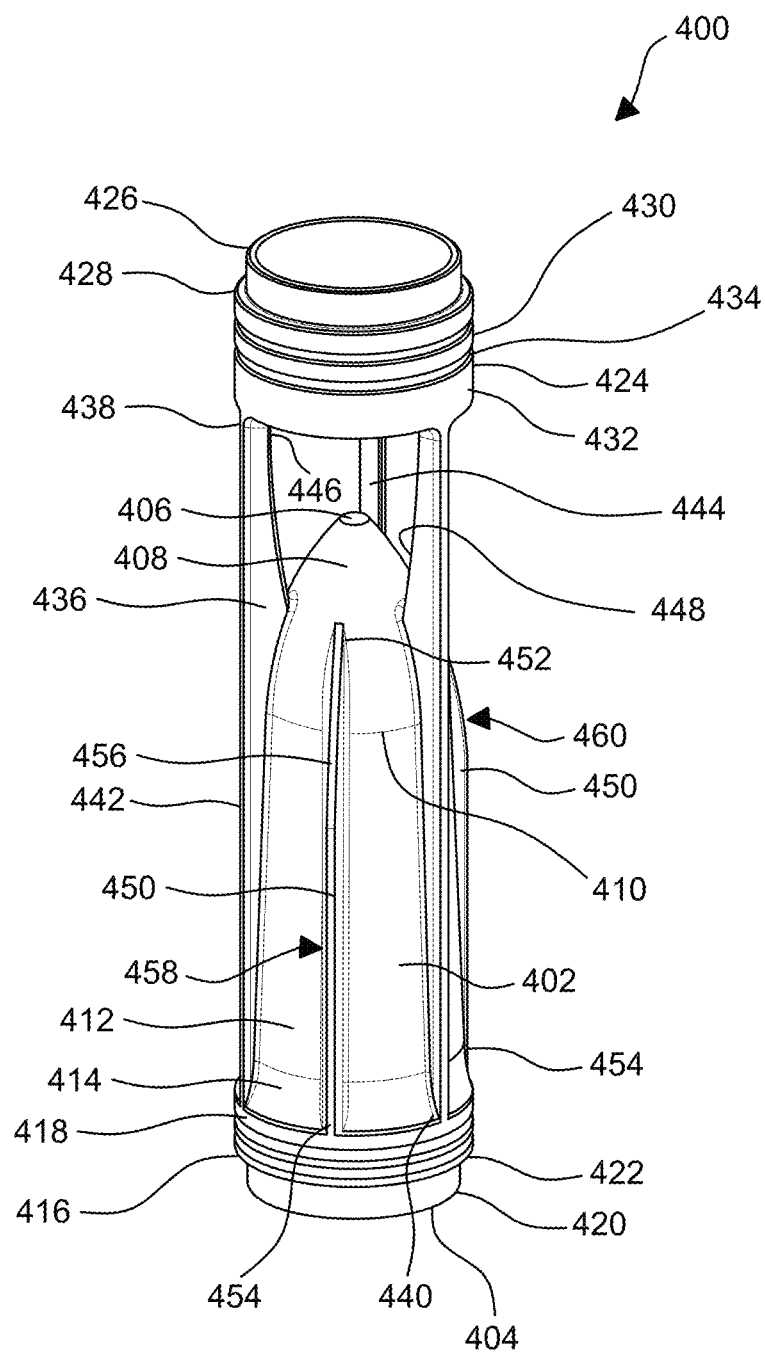
FIG. 4A is a perspective view of a flow distribution structure, in accordance with an embodiment of the disclosure.

FIG. 4A is a perspective view of a flow distribution structure 400, in accordance with an embodiment of the disclosure. The flow distribution structure 400 includes a body 402 having a distal end 404 and a proximal end 406. In some embodiments, the body 402 is hollow from the distal end 404 to the proximal end 406. In other embodiments, the body 402 is solid or partially solid.

A tapered proximal portion 408 extends from the proximal end 406 towards the distal end 404. The tapered proximal portion 408 tapers from a transition 410 towards the proximal end 406. In one embodiment, the tapered proximal portion 408 tapers nonlinearly, for example exponentially. In another embodiment, the tapered proximal portion 408 tapers linearly.

The body 402 includes a substantially cylindrical portion 412 that is distal to the tapered proximal portion 408. In some embodiments, the substantially cylindrical portion 412 has a constant outer diameter. In some embodiments, the substantially cylindrical portion 412 changes in diameter over the length thereof. For example, the substantially cylindrical portion 412 reduces in diameter over the length thereof. The substantially cylindrical portion 412 begins at the transition 410 and ends at a flared portion 414. The flared portion 414 increases in diameter from the substantially cylindrical portion 412 towards the distal end 404.

Located between the flared portion 414 and the distal end 404 is a distal portion 416. The distal portion 416 includes a plurality of annular protrusions 418 and a reduced diameter portion 420 that forms a shoulder 422. The reduced diameter portion 420 and the shoulder 422 are configured to mate with a central opening 268 in the lower end cap 258.

An inlet 424 is spaced from the proximal end 406 of the body 402. The inlet 424 is configured for connecting with the central inlet opening 266 in the upper end cap 256 of the blood oxygenation device. The inlet 424 includes a reduced diameter portion 426 and a step 428 that is configured to mate with the central inlet opening 266 of the upper end cap 256. A plurality of annular protrusions 430 are located on a constant diameter portion 432 of the inlet 424. The annular protrusions 430 are separated by recesses or grooves 434 that surround the inlet 424.

The flow distribution structure 400 includes a plurality of dividers 436 positioned between the inlet 424 and the body 402. In one aspect, the plurality of dividers 436 includes at least 3 dividers spaced uniformly around the body 402. The plurality of dividers 436 include an outer edge 442 and an inner edge 444. The outer edge 442 includes a first end 438 that is joined to the inlet 424 and a second end 440 joined to the flared portion 414. In some embodiments, the outer edge 442 is substantially straight and aligns with an outer diameter of the inlet 424 and an outer diameter of the distal portion 416. In other embodiments, the outer edge 442 does not align with the outer diameter of the inlet 424 or the outer diameter of the distal portion 416. The inner edge 444 includes a first end 446 that is joined to the inlet 424 and a second end 448 that is joined to the tapered proximal portion 408. In various embodiments, the plurality of dividers are curved with respect to the longitudinal axis. In other embodiments, the plurality of dividers are not curved. In various embodiments, the thickness of the plurality of dividers 436 reduces from the tapered proximal portion 408 towards the inlet 424.

A plurality of ribs 450 are located uniformly around the body 402. The ribs 450 extend from the tapered proximal portion 408 towards the distal end 404. In one aspect, at least 3 ribs 450 are located on the flow distribution structure 400. A first end 452 of each of the plurality of ribs 450 is joined to the tapered proximal portion 408. A second end 454 of each of the plurality of ribs 450 is joined to the flared portion 414. The second end 454 of each of the plurality of ribs 450 are longitudinally aligned with the second end 440 of the outer edge 442 of the plurality of dividers 436. Each of the plurality of ribs 450 has an outer edge 456 that includes a substantially straight portion 458 that algins with the outer diameter of the distal portion 416, and a curved portion 460 that curves towards the tapered proximal portion 408. The uniform spacing of the plurality of dividers 436 and the plurality of ribs 450 around the body 402 creates liquid diversion channels between the dividers 436 and the ribs 450. As such, blood flowing over the body 402 is separated into multiple streams for introduction into the heat exchanger module 224.

Figure 4B:
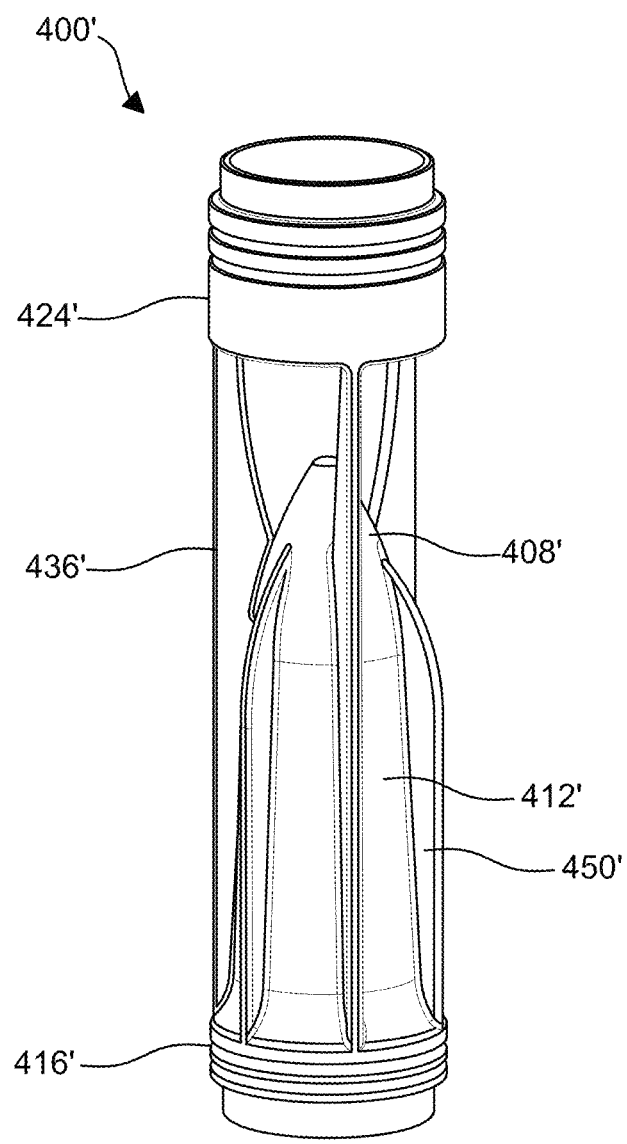
FIG. 4B is a perspective view of a flow distribution structure, in accordance with an embodiment of the disclosure.

FIG. 4B is a perspective view of a flow distribution structure 400', in accordance with an embodiment of the disclosure. The flow distribution structure 400' of FIG. 4B is substantially similar to the flow distribution structure 400 of FIG. 4A. However, the outer diameter of the substantially cylindrical portion 412' and the tapered proximal portion 408' are smaller. This configuration results in greater height of the plurality of dividers 436' and the plurality of ribs 450' above the surface of the substantially cylindrical portion 412' and the tapered proximal portion 408'. This allows for more defined liquid diversion channels to aid in separating blood flowing over the body 402' into multiple streams. A ratio of an outer diameter of the substantially cylindrical portion 412' to the outer diameter of the distal portion 416' or the outer diameter of the inlet 424' is less than 0.8 to 1 (<0.8:1). Conversely, in the flow distribution structure 400 of FIG. 4A, a ratio of an outer diameter of the substantially cylindrical portion 412 to the outer diameter of the distal portion 416 or the outer diameter of the inlet 424 is greater than 0.8 to 1 (>0.8:1).

Figure 5:
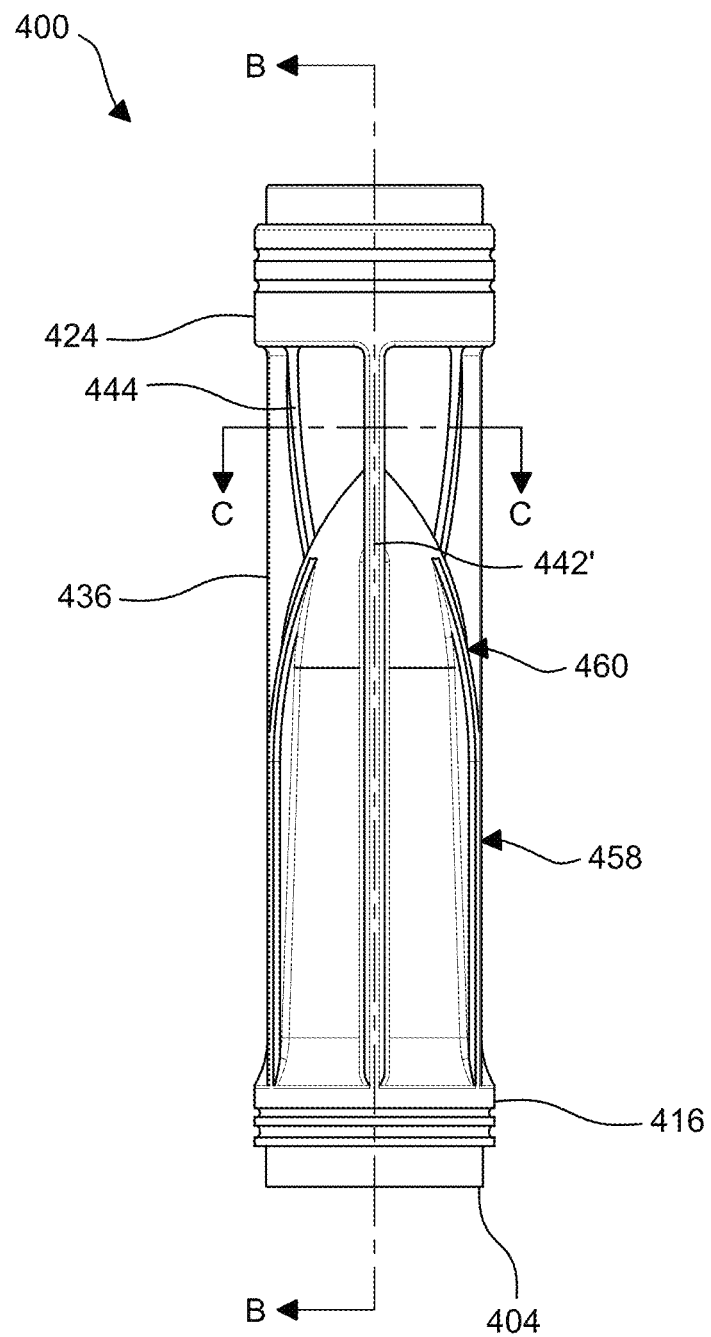
FIG. 5 is a side view of the flow distribution structure of FIG. 4A.

FIG. 5 is a side view of the flow distribution structure 400 of FIG. 4A. Visible in FIG. 5 at the center of the image is the outer edge 442 of the plurality of dividers 436 sharing the outside diameter of the inlet 424 and the distal portion 416.

Figure 6:
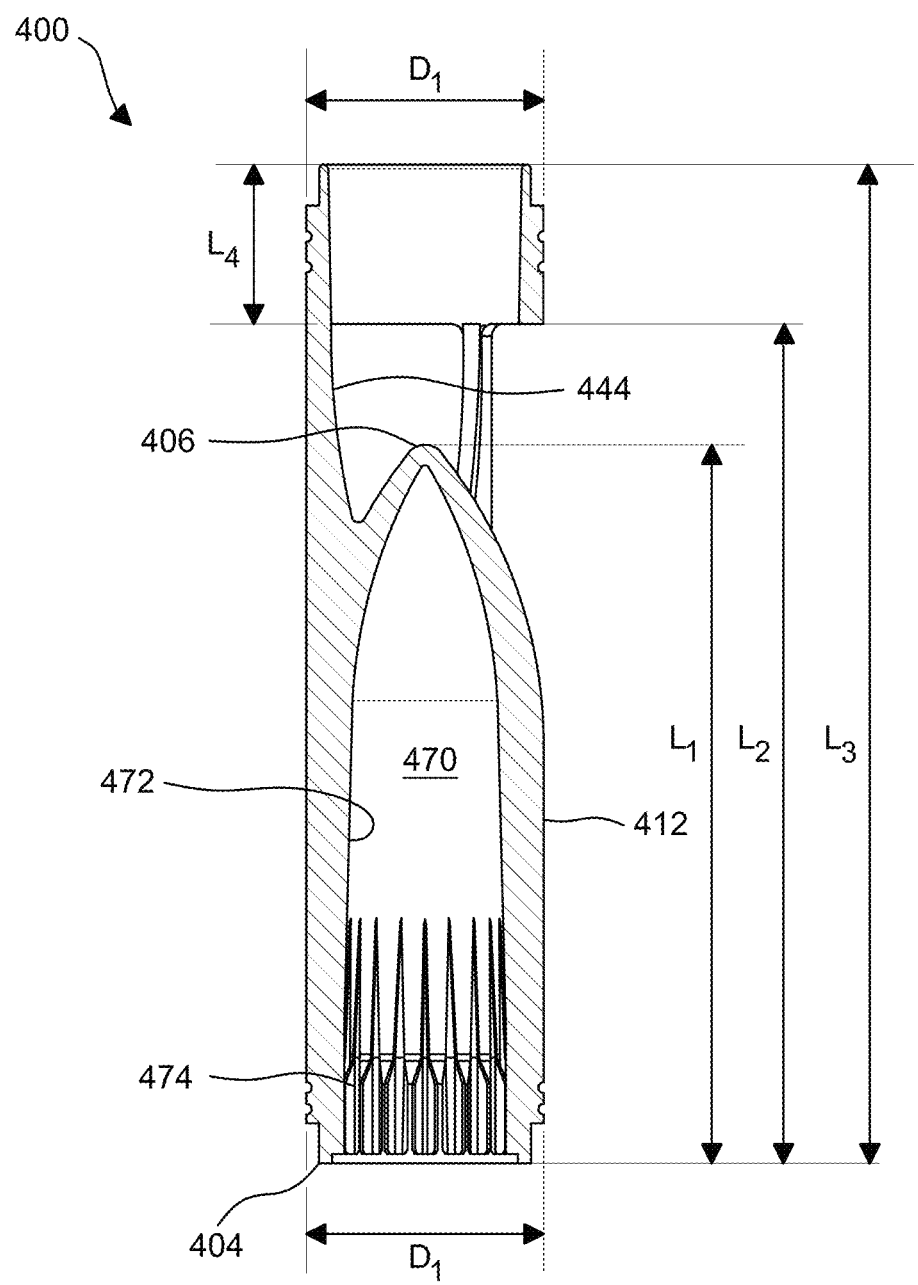
FIG. 6 is a cross-section of the flow distribution structure taken along line B-B of FIG. 5.

FIG. 6 is a cross-section of the flow distribution structure 400 taken along line B-B of FIG. 5. The interior of the body 402 is viewable in FIG. 6. A hollow cavity 470 extends from the distal end 404 to the proximal end 406. A plurality of ribs 474 are formed along an inner surface 472 of the hollow cavity 470. The plurality of ribs 474 are for connecting the flow distribution structure 400 to a fixture (e.g., a stand) to fix a location of the device that is convenient for the operator. In one embodiment, the plurality of ribs 474 are configured to mate with a fixing column (not shown) inserted into the flow distribution structure 400 to keep the device in place. The plurality of ribs 474 extend from the distal end 404 towards the proximal end 406. The plurality of ribs 474 end along the inner surface 472 inside of the substantially cylindrical portion 412.

As illustrated in FIG. 6, a length $L_1$ from the distal end 404 of the body 402 to the proximal end 406 of the body 402 is preferably in a range of about 67 mm to 77 mm, more preferably in a range of about 70 mm to 74 mm. In one embodiment, the length $L_1$ is 72 mm. A length $L_2$ from the distal end 404 of the body 402 to the first end 438 of the dividers 436 joined to the inlet 424 is preferably in a range of about 79 mm to 89 mm, more preferably in a range of about 82 mm to 86 mm. In one embodiment, the length $L_2$ is 84 mm. A length $L_3$ from the distal end 404 of the body 402 to the proximal end of the inlet 424 is preferably in a range of about 95 mm to 105 mm, more preferably in a range of about 98 mm to 102 mm. In one embodiment, the length $L_3$ is 100 mm. A length $L_4$ of the inlet 424 is preferably in a range of about 11 mm to 21 mm, more preferably in a range of about 14 mm to 18 mm. In one embodiment, the length $L_4$ is 16 mm. A diameter $D_1$ of the distal portion 416 of the body, the inlet 424, the outer edge 442 of the plurality of dividers 436, and the outer edge 456 of the plurality of ribs 450 is preferably in a range of about 19 mm to 29 mm, more preferably in a range of about 22 mm to 26 mm. In one embodiment, the diameter $D_1$ is 24 mm.

Figure 7:
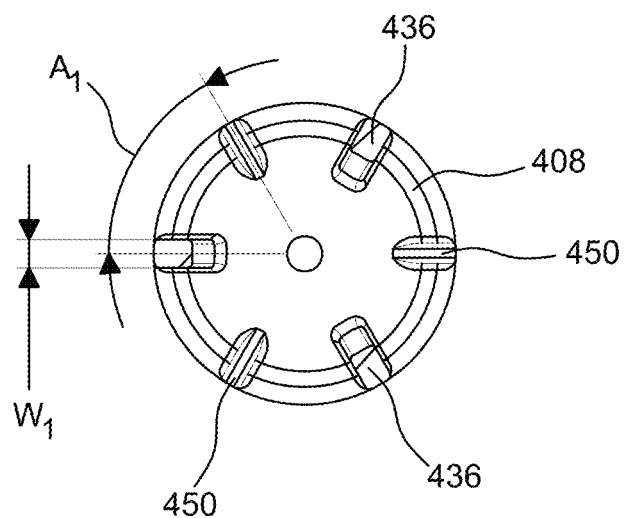
FIG. 7 is a cross-section of the flow distribution structure taken along line C-C of FIG. 5.

FIG. 7 is a cross-section of the flow distribution structure 400 taken along line C-C of FIG. 5. FIG. 7 shows the plurality of dividers 436 and the plurality of ribs 450 spaced uniformly on the tapered proximal portion 408. While three dividers 436 and three ribs are illustrated, some embodiments may include up to thirty dividers 436 and thirty ribs 450. The plurality of dividers 436 and the plurality of ribs 450 may be positioned radially around the tapered proximal portion 408 at an angle $A_1$ in a range of about 6 degrees to 60 degrees. Each of the plurality of dividers 436 and the plurality of ribs 450 may include a width $W_1$ in a range of about 1 mm to 7 mm, more preferably in a range of about 2.1 mm to 6 mm.

Figure 8:
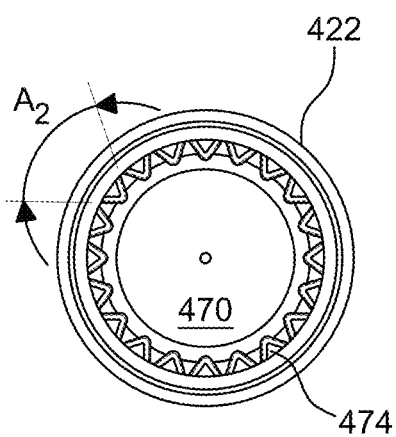
FIG. 8 is a bottom view of the flow distribution structure of FIG. 4A.

FIG. 8 is a bottom view of the flow distribution structure 400 of FIG. 4A. As illustrated, the plurality of ribs 474 form a ring and surround the entire inner surface 472 of the hollow cavity 470 adjacent the distal end 404. The ribs 474 are substantially triangular and form an angle $A_2$ in a range of about 69 degrees to 89 degrees, more preferably in the range of about 75 degrees to 83 degrees. In one embodiment the angle $A_2$ is about 79 degrees. The flow distribution structure 400 may include up to 40 ribs 474. Preferable, the flow distribution structure 400 includes between about 10 to 40 ribs, more preferably between about 15 to 25 ribs. In one embodiment, the flow distribution structure 400 includes 20 ribs.

Figure 9:
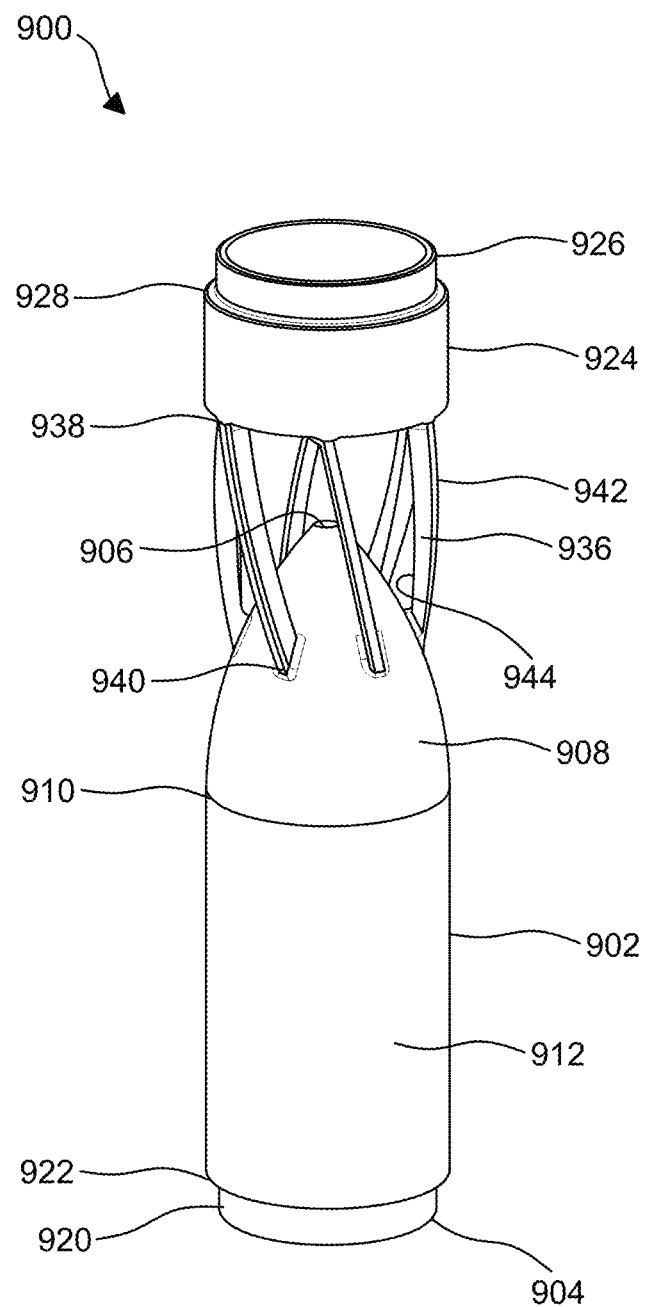
FIG. 9 is a perspective view of a flow distribution structure, in accordance with an embodiment of the disclosure.

FIG. 9 is a perspective view of a flow distribution structure, in accordance with embodiments of the disclosure. The flow distribution structure 900 includes a body 902 having a distal end 904 and a proximal end 906. In some embodiments, the body 902 is hollow from the distal end 904 to the proximal end 906. In other embodiments, the body 902 is solid or partially solid.

A tapered proximal portion 908 extends from the proximal end 906 towards the distal end 904. The tapered proximal portion 908 tapers from a transition 910 towards the proximal end 906. In one embodiment, the tapered proximal portion 908 tapers nonlinearly, for example exponentially. In another embodiment, the tapered proximal portion 908 tapers linearly. The body 902 includes a distal or substantially cylindrical portion 912 that is distal to the tapered proximal portion 908. In some embodiments, the substantially cylindrical portion 912 has a constant outer diameter. In some embodiments, the substantially cylindrical portion 912 changes in diameter over the length thereof. The substantially cylindrical portion 912 begins at the transition 910 and ends at a reduced diameter portion 920 that forms a shoulder 922. The reduced diameter portion 920 and the shoulder 922 are configured to mate with a central opening 268 in the lower cap 258. In various embodiments the length of the tapered proximal portion 908 is between about 30 to about 70 percent of the length of the distal portion 912. In certain embodiments, the length of the tapered proximal portion 908 is between about 40-60 percent of the length of the distal portion 912. In other embodiments, the length of the tapered proximal portion 908 is less than a length of the distal portion 912.

An inlet 924 is spaced from the proximal end 906 of the body 902. The inlet 924 is configured for connecting with a central inlet opening 266 in the upper end cap 256 of the blood oxygenation device. The inlet 924 includes a reduced diameter portion 926 and a step 928 that is configured to mate with the central inlet opening 266 of the upper end cap 256.

The flow distribution structure 900 includes a plurality of dividers 936 positioned between the inlet 924 and the body 902. In one aspect, the plurality of dividers 936 includes at least 6 dividers spaced uniformly around the body 902. The plurality of dividers 936 include an outer edge 942 and an inner edge 944. The plurality of dividers 936 have a consistent distance between the outer edge 942 and the inner edge 944 from a first end 938 that is joined to the inlet 924 and a second end 940 that is joined to the tapered proximal portion 908. In various embodiments, each of the plurality of dividers 936 curves, with respect to a longitudinal axis of the structure 900, from the first end 938 to the second end 940. The attachment point of the first end 938 to the inlet 924 is radially offset from that of the second end 940 to the tapered proximal portion 908, such that the plurality of dividers 936 spiral as they extend longitudinally from the inlet 924 to the portion 908. In some embodiments, the plurality of dividers 936 spiral in a clockwise direction from the inlet 924 towards the tapered proximal portion 908. In other embodiments, the plurality of dividers 936 spiral in a counter-clockwise direction from the inlet 924 towards the tapered proximal portion 908. In certain embodiments, the dividers are configured to extend in a generally parallel fashion. In other embodiments, the spacing between the first ends 938 is somewhat larger than the spacing between the second ends 940.

The plurality of dividers 936 create liquid diversion channels such that blood flowing over between the dividers 936 is separated into multiple streams for introduction into the heat exchanger module 224. In various embodiments, a plurality of six dividers 936 spiral in a clockwise direction from the inlet 924 towards the tapered proximal portion 908. A plurality of six dividers 936 reduce the need for deliberate alignment of the dividers 936 in relation to the blood inlet port 238 during the potting assembly phase of the oxygenator production which thereby simplifies the production process. In various embodiments, the dividers are configured to spiral in the direction of blood flow. In some embodiments, the length, curvature and radial offset of the dividers 936 are selected to match the flow characteristics of the incoming blood so as to reduce or minimize forces imparted on the incoming blood.

Figure 10:
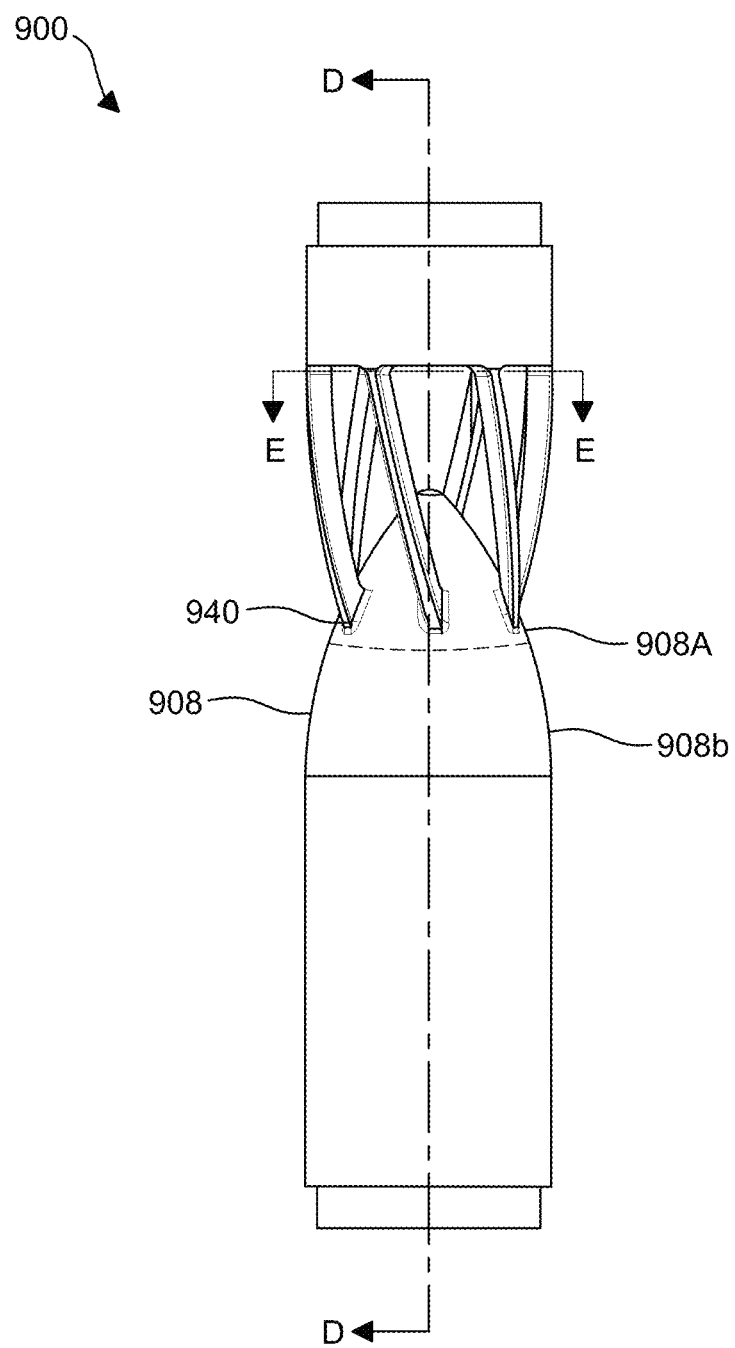
FIG. 10 is a side view of the flow distribution structure of FIG. 9.

FIG. 10 is a side view of the flow distribution structure 900 of FIG. 9. As illustrated in FIG. 10, the tapered proximal portion 908 includes an upper half 908a and a lower half 908b. The second end 940 of each of the plurality of curved dividers 936 is joined to the upper half 908a of tapered proximal portion 908. As shown in FIG. 9, the first end 938 and the second end 940 of the plurality of curved dividers 936 are longitudinally offset from one another. In various embodiments, each of the second ends 940 of the plurality of dividers 936 attaches to an approximate longitudinal midpoint of the tapered proximal portion 908. In other embodiments, the second ends 940 each attach in either the proximal third, the central third or the distal third of the tapered proximal portion 908. In exemplary embodiments, the radial offset (between the first end 938 and the second end 940) is between about 5 and about 50 degrees (about the circumference). In other embodiments, this radial offset is between about 10 and about 30 degrees.

Figure 11:
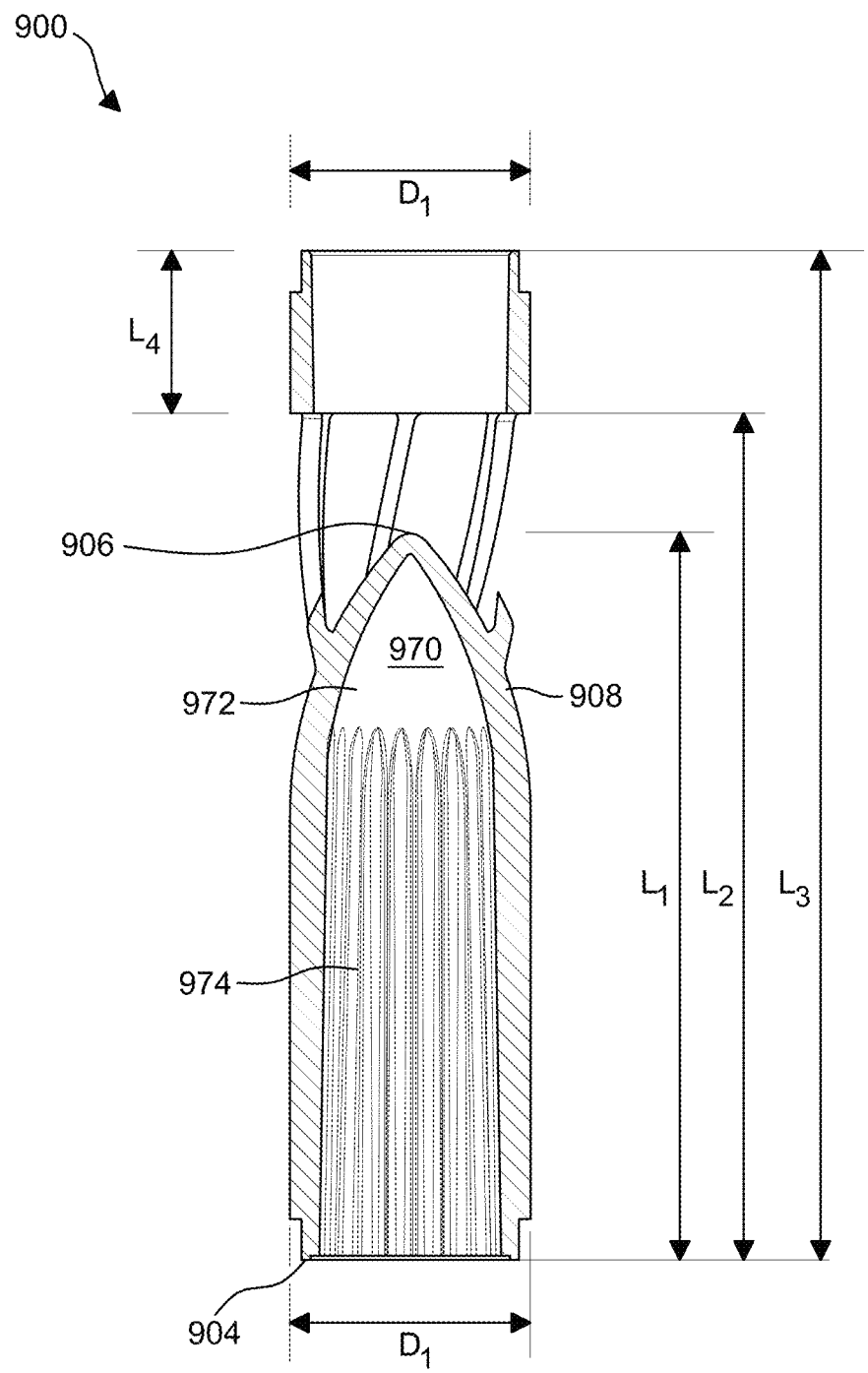
FIG. 11 is a cross-section of the flow distribution structure taken along line D-D of FIG. 10.

FIG. 11 is a cross-section of the flow distribution structure taken along line D-D of FIG. 10. The interior of the body 902 is viewable in FIG. 11. A hollow cavity 970 extends from the distal end 904 to the proximal end 906. A plurality of ribs 974 are formed along an inner surface 972 of the hollow cavity 970. The plurality of ribs 974 are for connecting the flow distribution structure 900 to fix a location of the device that is convenient for the operator. In one embodiment, the plurality of ribs 974 are configured to mate with a fixing column (not shown) inserted into the flow distribution structure 900 to keep the device in place. The plurality of ribs 974 extend from the distal end 904 towards the proximal end 906. The plurality of ribs 974 end along the inner surface 972 to an inner surface of a tapered proximal portion 908.

A length $L_1$ from the distal end 904 of the body 902 to the proximal end 906 of the body 902 is preferably in a range of about 67 mm to 77 mm, more preferably in a range of about 70 mm to 74 mm. In one embodiment, the length $L_1$ is 72 mm. A length $L_2$ from the distal end 904 of the body 902 to the first end 938 of the dividers 936 joined to the inlet 924 is preferably in a range of about 79 mm to 89 mm, more preferably in a range of about 82 mm to 86 mm. In one embodiment, the length $L_2$ is 84 mm. A length $L_3$ from the distal end 904 of the body 902 to the proximal end of the inlet 924 is preferably in a range of about 95 mm to 105 mm, more preferably in a range of about 98 mm to 102 mm. In one embodiment, the length $L_3$ is 100 mm. A length $L_4$ of the inlet 924 is preferably in a range of about 11 mm to 21 mm, more preferably in a range of about 14 mm to 18 mm. In one embodiment, the length $L_4$ is 16 mm. A diameter $D_1$ of the substantially cylindrical portion 912 and the inlet 924 is preferably in a range of about 19 mm to 29 mm, more preferably in a range of about 22 mm to 26 mm. In one embodiment, the diameter $D_1$ is 24 mm.

Figure 12:
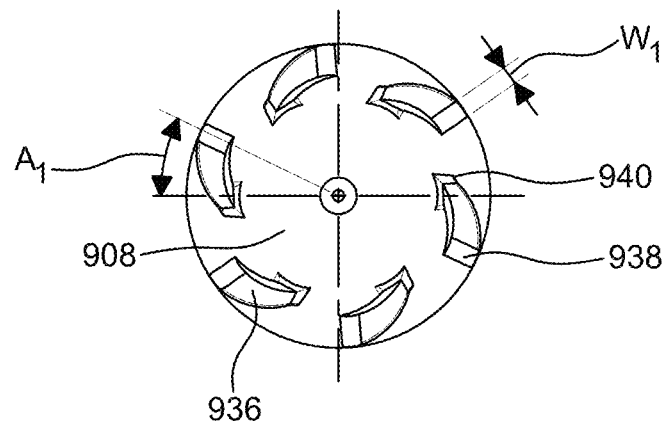
FIG. 12 is a cross-section of the flow distribution structure taken along line E-E of FIG. 10.

FIG. 12 is a cross-section of the flow distribution structure 900 taken along line E-E of FIG. 10. FIG. 12 shows the plurality of dividers 936 spaced uniformly about the tapered proximal portion 916. While six dividers 936 are illustrated, some embodiments may include more dividers 936, for example, up to thirty dividers 936. Clearly shown in FIG. 12, is the spiral of the plurality of dividers 936. The first end 938 and the second end 940 of the plurality of curved dividers 936 are both longitudinally offset from one another and radially offset from one another. The plurality of dividers 936 form a spiral that has an angle $A_1$ in the range of 5 degrees to 50 degrees. Each of the plurality of dividers 936 may include a width $W_1$ in a range of about 0.5 mm to 3 mm, more preferably in a range of about 1 mm to 2 mm. In one embodiment, the plurality of dividers 936 include a width $W_1$ of 1.53 mm.

Figure 13:
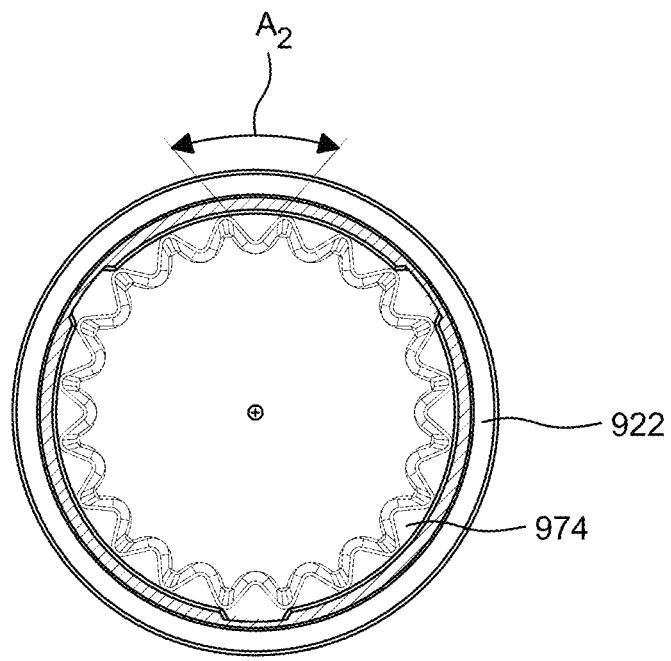
FIG. 13 is a bottom view of the flow distribution structure of FIG. 9.

FIG. 13 is a bottom view of the flow distribution structure 900 of FIG. 9. As illustrated, the plurality of ribs 974 form a ring and surround the entire inner surface 972 of the hollow cavity 970 adjacent the distal end 904. The ribs 974 are substantially triangular and form an angle $A_2$ in a range of about 69 degrees to 89 degrees, more preferably in the range of about 75 degrees to 85 degrees. In one embodiment the angle $A_2$ is about 80 degrees. The flow distribution structure 900 may include up to 40 ribs 974. Preferable, the flow distribution structure 900 includes between about 10 to 40 ribs, more preferably between about 15 to 25 ribs. In one embodiment, the flow distribution structure 900 includes 20 ribs.

Performance Testing of Flow Distribution Structures in Gas Exchange In Vitro Testing of an Oxygentor Gas Transfer characteristics of an oxygenator were determined in vitro in accordance with ISO 7199-2017. $O_2$ and $CO_2$ transfer rate were used as indices of gas transfer characteristics of oxygenators having flow control structures in accordance with FIG. 4A, FIG. 4B, and FIG. 9.

Each test used a large aliquot of freshly collected heparinized animal (bovine) blood. Blood and gas were circulated through the test unit at various flow rates (and particularly at maximum values). When venous inlet conditions were stable and venous blood had certain parameter values within the ranges fixed by the ISO std, samples were collected at inlet and outlet of the test unit. They were analyzed for $O_2$ saturation, Hb concentration, and $O_2$ and $CO_2$ partial pressures on a blood gas analyzer. $CO_2$ concentration was measured at the gas outlet using a capnometer. These parameters allowed for the calculation of $O_2$ and $CO_2$ transfer rates. Blood and gas pressures at inlet and outlet of the test unit were measured by means of pressure sensors: the inlet-outlet difference provided the DeltaP across the unit which has great effect in determining the red cell stress level (increasing with DeltaP).

In general, the most challenging in vitro test situation for an oxygenator is at maximum blood flow rate and 1:1 ratio with gas flow rate. In such condition, the $O_2$ and $CO_2$ transfer rates, the arterial $O_2$ partial pressure and the blood DeltaP are measured and considered for evaluating the oxygenator efficiency in clinical use. The best result is achieved when $O_2$ and $CO_2$ transfer rates ($O_2$TR and $CO_2$TR) and arterial $O_2$ partial pressure (art$O_2$pp) are high and DeltaP is low.

The test results for oxygenators having flow control structures in accordance with FIG. 4A, FIG. 4B and FIG. 9, at a blood flow rate of 7.0 L/minute are shown below:

| Oxygenator | O₂TR (ml/L) | CO₂TR (ml/L) | artO₂pp (mmHG) | DeltaP (mmHg) |
|---|---|---|---|---|
| FIG. 4A | 56 | 45 | 118 | 44 |
| FIG. 4B | 54 | 42 | 80 | 85 |
| FIG. 9 | 58 | 46 | 138 | 56 |

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A blood processing unit for use in connection with extracorporeal blood circulation, the device comprising:
   a housing including a blood inlet, an upper end cap defining a central inlet opening, and a blood outlet, wherein blood flows along a blood flow path between the blood inlet and the blood outlet;
   a plurality of layers of hollow fibers disposed inside the housing and along the blood flow path, the hollow fibers fluidly coupled to a gas inlet port and a gas outlet port;
   a flow distribution structure for modifying blood flowing along the blood flow path, the structure comprising:
      a body having a distal end, a proximal end, and an outer surface extending between the distal end and the proximal end, wherein the body includes a tapered proximal portion extending from the proximal end towards the distal end, the tapered proximal portion having an upper half and a lower half;
      an inlet spaced from the proximal end, the inlet configured for connecting with the upper end cap; and
      a plurality of curved dividers coupled to and extending between the inlet and the tapered proximal portion, the plurality of curved dividers each including a first end connected to the inlet and a second end connected to the body,
      wherein the second end of each of the plurality of curved dividers is joined to the tapered proximal portion upper half.

2. The device of claim 1, wherein the body further includes a distal portion and a first length of the tapered proximal portion is less than a second length of the distal portion.

3. The device of claim 2, wherein the plurality of curved dividers spiral in the direction of blood flow from the inlet towards the tapered proximal portion.

4. The device of claim 3, wherein the spiral has an angle in the range of 5 degrees to 50 degrees.

5. The device of claim 3, wherein the tapered proximal portion tapers non-linearly.

6. The device of claim 1, wherein the inlet includes a reduced diameter portion and a step configured to mate with the central inlet opening of the upper end cap.

7. The device of claim 1, wherein the body defines an inner surface extending longitudinally from the distal end toward the proximal end.

8. The device of claim 7, wherein the inner surface of the body includes a plurality of ribs for connecting the flow distribution structure to a fixture for fixing a location of the blood processing unit.

9. The device of claim 8, wherein the plurality of ribs extend from the distal end to an inner surface of the tapered proximal portion.

10. The device of claim 1, wherein the plurality of dividers includes at least three dividers.

11. The device of claim 1, wherein the second end of each of the plurality of curved dividers is joined to the proximal third of the tapered proximal portion.

12. A flow distribution structure for use with a blood oxygenation device, the structure comprising:
   a body having a distal end, a proximal end, and a tapered proximal portion extending from the proximal end towards the distal end, the tapered proximal portion having an upper half and a lower half;
   an inlet spaced from the proximal end, the inlet configured for connecting with an upper end cap of the blood oxygenation device; and
   a plurality of curved dividers positioned between the inlet and the body, each of the plurality of curved dividers include a first end connected to the inlet and a second end connected to the body, wherein the plurality of dividers spiral from the inlet towards the tapered proximal portion;
   wherein the second end of each of the plurality of curved dividers is joined to the tapered proximal portion upper half; and
   wherein blood flows through the inlet and over an outer surface of the body.

13. The structure of claim 12, wherein the spiral has an angle in the range of 5 degrees to 50 degrees.

14. The structure of claim 12, wherein an inner surface of the body includes a plurality of ribs for connecting the flow distribution structure to a fixture for fixing a location of the blood processing unit.

15. The structure of claim 12, wherein the second end of each of the plurality of curved dividers is joined to the proximal third of the tapered proximal portion.

16. The structure of claim 12, wherein the plurality of curved dividers spiral in the direction of blood flow from the inlet towards the tapered proximal portion.

17. The structure of claim 12, wherein a body length from the distal end of the body to the proximal end of the body is in a range of from 67 to 77 mm.

18. The structure of claim 17, wherein a length from the distal end of the body to a first end of the curved dividers in in a range of from 79 to 89 mm.

* * * * *